United States Patent [19]
Gerstein

[11] Patent Number: 5,391,368
[45] Date of Patent: Feb. 21, 1995

[54] HAIR STYLING SHAMPOOS

[75] Inventor: Terry Gerstein, East Brunswick, N.J.

[73] Assignee: Revlon Consumer Products Corporation, New York, N.Y.

[21] Appl. No.: 103,615

[22] Filed: Aug. 9, 1993

[51] Int. Cl.⁶ ............................................. A61K 7/075
[52] U.S. Cl. ........................... 424/70.13; 252/174.23; 252/DIG. 13; 424/71; 424/DIG. 2; 424/70.11; 424/70.15; 424/70.16; 424/70.17
[58] Field of Search ...................... 424/70, 71, DIG. 2, 424/401; 252/DIG. 13, 174.23

[56] References Cited

U.S. PATENT DOCUMENTS

| | | | |
|---|---|---|---|
| 3,990,991 | 11/1976 | Gerstein | 252/542 |
| 3,996,146 | 12/1976 | Tarasov et al. | 252/142 |
| 4,009,256 | 2/1977 | Nowak, Jr. et al. | 424/70 |
| 4,732,692 | 3/1988 | Zabolto | 252/106 |
| 4,832,872 | 5/1989 | Scandel | 252/547 |
| 5,057,311 | 10/1991 | Kamegai | 424/70 |
| 5,118,498 | 6/1992 | Helioff et al. | 424/70 |
| 5,120,532 | 6/1992 | Wells | 424/70 |
| 5,217,652 | 6/1993 | Iouanni | 252/547 |

FOREIGN PATENT DOCUMENTS 9210162  6/1992  WIPO .

Primary Examiner—Thurman K. Page
Assistant Examiner—Robert H. Harrison
Attorney, Agent, or Firm—Julie Blackburn

[57] ABSTRACT

An aqueous composition free of nonaqueous solvents for cleansing, conditioning and styling the hair comprising:
(a) 3-40% anionic surfactant,
(b) 0.5-20% amphoteric surfactant,
(c) 0.1-15% hair styling polymer,
(d) 0.001-5% of a cationic conditioning polymer; and
(e) 40-95% water.

8 Claims, No Drawings

HAIR STYLING SHAMPOOS

TECHNICAL FIELD

The invention is in the field of surfactant containing cosmetic compositions for cleansing, conditioning, and styling the hair.

BACKGROUND OF THE INVENTION

Maintenance of the hair consists of washing, conditioning, and styling hair on a regular basis. Traditionally this has been a three step process. Shampoo is first used to cleanse the hair. After the hair is rinsed clean, a second conditioning product is applied and allowed to penetrate the hair for a specified period of time. These conditioning products usually contain cationic conditioning agents which remain bound to the hair fiber after the conditioner is rinsed out. The cationic agents form an insulating coat on the hair shaft resulting in hair with enhanced shine and combability. The third, optional step involves applying a styling aid to the clean hair to assist in arranging the hair into the desired configuration. Many different styling aids are available, including gel, mousse, hairspray, etc.

Within the last decade, cosmetics companies have focused on introducing products which perform more than one function. For example, shampoos are now available which cleanse and condition the hair in one step, thus eliminating the need for two separate products and two separate applications. The popular two-in-one shampoos are formulated with three essential ingredients besides water: an anionic surfactant, an insoluble nonvolatile silicone, and a suspending agent for the silicone. The silicones deposit on the hair to form a protective film which makes the hair softer, and improves combability and sheen. These shampoos do have certain disadvantages. The insoluble silicone, by reducing the inter-fiber frictional forces, reduces the ability of the hair to hold a curl. In addition, habitual use of these two-in-one shampoos causes a silicone film to build up on the hair. This silicone film is known to interfere with the effectiveness of other hair treatment procedures such as perming, coloring, or straightening. Although these two-in-one shampoos are very popular, their inherent disadvantages make it desireable to formulate shampoos which provide two-in-one conditioning without sacrificing the effectiveness of styling, perming, coloring or straightening treatments.

Other types of two-in-one shampoos achieve conditioning effects with cationic conditioning polymers rather than silicones. However, the incompatibility between cationic hair conditioning polymers and anionic surfactants is well known in the art, so shampoos which achieve conditioning by the incorporation of cationic polymers often use nonionic or amphoteric surfactants instead of the traditional anionic surfactants. The resulting shampoos are less than desireable for commercial purposes because anionic surfactants generally produce copious foam while nonionic and amphoteric surfactants do not. In reality there is no positive correlation between the amount of foam a shampoo produces and the degree to which it cleanses. Unfortunately, however, consumers equate foaming with cleansing, and shampoos which do not foam well are perceived to be less effective in cleansing performance.

Other types of dual function shampoos which provide cleansing and hair setting features are known. These shampoos contain some of the hair setting resins traditionally found in styling aids, the end result being a shampoo which cleanses and provides a subtle, temporary set to the hair after shampooing. In particular, U.S. Pat. No. 5,118,498 to Helioff, discloses hair setting shampoo compositions which contain anionic surfactants, water, and an alcoholic solution of the ethyl butyl alkyl half ester of a $C_{1-5}$ alkyl vinyl ether maleic anhydride copolymer. This resin is known by the trade name "Gantrez". Most hair setting polymers have relatively low water solubility so they are either sold in a solvent solution which, when added to the shampoo composition enhances solubility, or, in the alternative, solvents must be added to the shampoo composition to facilitate solubility of the hair setting polymers. There are many disadvantages to putting solvents such as alcohol into shampoo compositions. Most solvents are foam depressants and tend to be drying to the hair. Because of consumer perceptions foam quantity is an important factor in commercial success of shampoos. Second, hair setting resins which are supplied in alcohol are more expensive than resins which are supplied in the powder form or dissolved in water.

For the above reasons it is of interest to formulate three in one shampoos which cleanse, condition, and provide a subtle set to the hair in one step, and at the same time are free of nonaqueous solvents. It is essential that these shampoos provide comparable if not superior cleansing, conditioning, and styling properties without the disadvantages of the prior art products.

SUMMARY OF THE INVENTION

The invention is directed to an aqueous composition free of nonaqueous solvents for cleansing, conditioning and styling the hair comprising:

(a) 3–40% anionic surfactant,
(b) 0.5–20% amphoteric surfactant,
(c) 0.1–15% hair styling polymer,
(d) 0.001–5% of a cationic conditioning polymer; and
(e) 40–95% water.

DETAILED DESCRIPTION

It has most unexpectedly been discovered that the above formulation provides a three-in-one shampoo which cleanses, conditions, and provides styling benefits in one application and is at the same time free of nonaqueous solvents. In prior art compositions the addition of solvents was essential to enhance solubility of the hair styling polymer in the aqueous shampoo composition. However, the invention is based upon the discovery that the addition of amphoteric surfactants to the shampoo composition in a certain ratio enables the solubilization of the hair styling polymer without the use of nonaqueous solvents.

The term "nonaqueous solvents" means organic solvents such as aromatic or aliphatic alcohols such as ethanol, propanol, butanol, benzyl alcohol, phenoxyethanol, propylene glycol, abietyl alcohol, butoxydiglycol, butoxyethanol, butylene glycol, dipropylene glycol, ethoxydiglycol, ethoxyethanol, glycol, hexyl alcohol, hexylene glycol, methanol, panthenol, or mixtures thereof. Anionic surfactants suitable for use with the invention can be broadly characterized as being derivatives of aliphatic acids containing a long hydrocarbon chain (typically from 8 to 22 carbons) and an anionic hydrophilic group such as a carboxy group, a sulfonate group, a sulfate group, etc. Suitable anionic surfactants in accordance with the invention include alkyl and alkyl ether sulfates of the formulas $ROSO_3M$ and $RO(C_2H_4O)_xSO_3M$, wherein R is alkyl or alkenyl of from about 8 to 22 carbon atoms, x is 1 to 12, and M is a water soluble cation such as ammonium, sodium, potassium, or triethanolamine. Also suitable are the water soluble salts of organic, sulfuric acid reaction products of the formula $R_1-SO_3-M$ wherein $R_1$ is a straight or branched chain saturated aliphatic hydrocarbon radical having 8 to 24 carbon atoms. Other anionics include reaction products of coconut oil derived fatty acids or other long hydrocarbon chain fatty acids esterified with isethionic acid and neutralized with sodium hydroxide as well as salts of alkyl sulfosuccinates, olefin sulfonates having about 12 to 24 carbons, and B-alkyloxy alkane sulfonates. Still, other anionic surfactants include the salts of long chain alkoyl sarcosinates, glutamates, and methyl taurates.

Preferred are alkyl and alkyl ether sulfates of the formulas $ROSO_3M$ and $RO(C_2H_4O)_xSO_3M$, wherein R is alkyl or alkenyl of from about 8 to 22 carbon atoms, x is 1 to 12, and M is a water soluble cation such as ammonium, sodium, potassium, or triethanolamine. Particularly preferred are lauryl sulfates and lauryl ether sulfates.

Suitable amphoteric surfactants include $C_{8-22}$ alkyl glycinates, propionates, imidazolines, and amphoalkylsulfonates sold under the registered trademark of "Miranol" by Miranol, Inc., Dayton Ohio. Examples of these surfactants are cocoamphoglycinate, cocoamphocarboxyglycinate, lauramphocarboxyglycinate, cocoamphopropionate, lauramphopropionate, stearamphoglycinate, cocoamphocarboxypropionate, tallowamphopropionate, tallowamphoglycinate, oleoamphocglycinate, caproamphoglycinate, caprylamphopropionate, caprylamphocarboxyglycinate, cocoyl imidazoline, lauryl imidazoline, stearyl imidazoline, behenyl imidazoline, behenylhydroxyethyl imidazoline, caprylamphopropylsulfonate, cocoamphopropylsulfonate, stearamphopropylsulfonate, oleoamphopropylsulfonate and the like.

Examples of amphoteric betaines and sultaines are $C_{12}$ to $C_{22}$ alkyl betaines and sultaines sold under the trademarks "Mirataine" by Miranol, Inc. and "Lonzaine" by Lonza, Inc. of Fairlawn, N.J. Examples of betaines and sultaines are cocobetaine, cocoamidoethyl betaine, cocoamidopropyl betaine, lauryl betaine, lauramidopropyl betaine, palmamidopropyl betaine, stearamidopropyl betaine, stearyl betaine, coco-sultaine, lauryl sultaine, tallowamidopropyl hydroxysultaine and the like.

Amine oxide surfactants which can adopt positive charges are also suitable and include $C_{12}$ to $C_{22}$ alkyl amine and amidoamine oxides.

Cationic polymers in accordance with the invention can be cationic cellulose derivatives, cationic starches, copolymers of a diallyl quaternary ammonium salt and acrylamide, quaternarized polyvinylpyrrolidone deriviatives, quaternarized vinylpyrrolidone vinylimidazol polymers, polyglycol amide condensates, quaternarized collagen polypeptide, polyethylene imine, cationized silicon polymer, cationic silicon polymers, copolymers of adipic acid and dimethylaminohydroxypropyl diethylenetriamine, polyaminopolyamide and their crosslinked water soluble polymers, cationic chitin derivatives, cationized guar gums and so on. Preferred cationic polymers are derivatives of polymeric saccharides such as cationized guar gums and particularly Polyquaternium-10 which is a modified cationic hydroxyethylcellulose sold under the tradename "UCARE" Polymer by Union Carbide Corporation.

Suitable hair styling polymers include acrylamide/sodium acrylate copolymer, acrylate/ammonium methacrylate copolymer, acrylic/acrylate copolymer, allyl steareate/VA copolymer, aminoethylacrylate phosphate/acrylate copolymer, allyl stearate/VA copolymer, butyl ester of ethylene/maleic anhydride copolymer, isopropyl ester of PVM/MA copolymer, octyacrylamide/acrylate/butylaminoethyl methacrylate copolymer, octyacrylamide/acrylates copolymer, polyethylacrylate, PVM/MA copolymer, PVP, PVP/eicosene copolymer, PVP/ethyl methacrylate/methacrylic acid copolymer, PVP/hexadecene copolymer, PVP/VA copolymer, stearylvinyl ether/maleic anhydride copolymer, vinyl acetate/crotonic acid copolymer, vinyl acetate/crotonic acid/vinyl neodecanoate copolymer, or mixtures thereof.

The preferred ratio of amphoteric surfactant to hair styling polymer may range from 1–20 parts:20–1 parts respectively, preferably 4 to 1:0.1–5 although a 1:1 ratio is preferred because it provides optimum solubility of the hair styling polymer in the shampoo composition.

In the preferred formulation of the invention the anionic surfactants are the alkyl and alkyl ether sulfates of the formulas $ROSO_3M$ and $RO(C_2H_4O)_xSO_3M$, wherein R is alkyl or alkenyl of from about 8 to 22 carbon atoms, x is 1 to 12, and M is a water soluble cation such as ammonium, sodium, potassium, or triethanolamine. Most preferred are sodium lauryl sulfate and sodium lauryl ether sulfate.

The preferred amphoteric surfactants are cocoamphoglycinate, cocoamphocarboxyglycinate, lauramphocarboxyglycinate, cocoamphopropionate, lauramphopropionate, stearamphoglycinate, cocoamphocarboxypropionate, tallowamphopropionate, tallowamphoglycinate, oleoamphoglycinate, caproamphoglycinate, caprylamphopropionate, caprylamphocarboxyglycinate, cocoyl imidazoline, lauryl imidazoline, stearyl imidazoline, behenyl imidazoline, behenylhydroxyethyl imidazoline, caprylamphopropylsulfonate, cocoamphpropylsulfonate, stearamphopropylsulfonate, oleoamphopropylsulfonate or mixtures thereof with cocoamphodipropionate most preferred.

The preferred hair styling polymers are butyl ester of PVM/MA copolymer, ethyl ester of PVM/MA copolymer octylacrylamide/acrylates/butylaminoethyl methacrylate copolymer, octylacrylamide/acrylates copolymer, PVM/MA copolymer, PVP/VA copolymer, vinyl acetate/crotonic acid/vinyl neodecanoate copolymer, vinyl acetate/crotonic acid copolymer, or mixtures thereof.

The preferred cationic polymers are cationic derivatives of guar gum such as guar hydroxypropyltrimonium chloride; those of hydroxyethyl cellulose, Polyquaternium 10, or other polymeric saccharidic derivatives.

The shampoo compositions of the invention are made by combining the ingredients in the usual manner and mixing thoroughly.

The invention will be further described in connection with the following examples which are set forth for the purposes of illustration only.

EXAMPLE 1

The basic invention is illustrated with the following simple formula:

| | w/w % |
|---|---|
| Sodium lauryl ether sulfate (28%) | 50.00 |
| Miranol C2M - SF Conc. (70%)* | 8.00 |
| Amphomer resin (National Starch) | 3.00 |
| Water qs | 100.00 |

*cocoamphodipropionate, Rhone Poulenc Corp.

The Amphomer polymer appears insoluble in the lauryl sulfate system unless the amphoteric is present. The amphoteric surfactant dissolves the Amphomer polymer and provides a unitary clear phase.

EXAMPLE 2

A shampoo composition in accordance with the invention was made as follows:

| | w/w% |
|---|---|
| Water | 35.03 |
| Miranol C2M - SF Conc. (70%) | 8.00 |
| Amphomer LMW | 3.00 |
| Sodium lauryl ether sulfate | 50.00 |
| Preservative | 0.04 |
| Acculyn 22 (30%)* | 3.33 |
| Fragrance | 0.60 |

*acrylates/steareth/methacrylate copolymer, Rohm & Haas Co.

The ingredients were combined and mixed to yield the shampoo composition.

EXAMPLE 3

A shampoo composition in accordance with the invention was made as follows:

| | w/w % |
|---|---|
| Sodium lauryl ether sulfate | 50.00 |
| Amophomer LMW | 3.00 |
| Miranol C2M - SF Conc. (70%) | 8.00 |
| Hydrolyzed animal protein | 0.04 |
| Fragrance | 0.75 |
| Polymer JR-30M* | 0.75 |
| Water qs | 100.00 |

*Polyquaternium-10, Union Carbide.

The above shampoo composition was made in accordance with Example 2.

EXAMPLE 4

The composition of Example 3 was compared to Revlon Flex Shampoo for lather, hair conditioning, and hair styling properties. A hair tress of virgin dark brown was shampooed with the composition of Example 3. An identical tress was shampooed with Revlon Flex Shampoo. The tresses were rinsed with water and rolled with a curler to dry. The results are compared below:

tress shampooed with Flex: The shampoo provided luxuriant foam which easily rinsed from the hair. The tress was more difficult to comb through when wet. After the curler was removed the curl was loose, less controlled.

tress shampoo with Example 3 composition: The shampoo provided luxuriant foam which easily rinsed from hair. The wet hair tress felt silky and slick and was easy to comb through. Upon removal of the curler, the dry curl was eceedingly tight and springy. The hair set was considerably better than that found in the hair tress treated with Flex.

CONCLUSION: The hair shampoo composition of the invention provides good foam, good conditioning, and imparts a subtle set to the hair.

What is claimed is:

1. An aqueous composition for cleansing, conditioning, and styling the hair comprising:
   (a) 3–40% anionic surfactant,
   (b) 0.5–20% amphoteric surfactant,
   (c) 0.1–15% hair styling polymer,
   (d) 0.001–5% of a cationic conditioning polymer; and
   (e) 40–95% water wherein said composition is free of nonaqueous solvents and the ratio of amphoteric surfactant to hair styling polymer is 1-20:20-1 respectively and the amphoteric surfactant solubilizes the hair styling polymer.

2. The composition of claim 1 wherein the anionic surfactant is one or more of an alkyl or alkyl ether sulfate of the formulas $ROSO_3M$ and $RO(C_2H_4O)_xSO_3M$ wherein R is alkyl or alkenyl of from about 8 to 22 carbon atoms, x is 1 to 12, and M is a water soluble cation which is ammonium, sodium, potassium, or triethanolamine.

3. The composition of claim 2 wherein the amphoteric surfactant is cocoamphoglycinate, cocoamphocarboxyglycinate, lauramphocarboxyglycinate, cocoamphopropionate, lauramphopropionate, stearamphoglycinate, cocoamphocarboxypropionate, tallowamphopropionate, tallowamphoglycinate, oleoamphocglycinate, caproamphoglycinate, caprylamphopropionate, caprylamphocarboxyglycinate, cocoyl imidazoline, lauryl imidazoline, stearyl imidazoline, behenyl imidazoline, behenylhydroxyethyl imidazoline, caprylamphopropylsulfonate, cocoamphopropylsulfonate, stearamphopropylsulfonate, oleoamphopropylsulfonate or mixtures thereof.

4. The composition of claim 3 wherein the hair styling polymer is butyl ester of PVM/MA copolymer, ethyl ester of PVM/MA copolymer octylacrylamide/acrylates/butylaminoethyl methacrylate copolymer, octylacrylamide/acrylates copolymer, PVM/MA copolymer, PVP/VA copolymer, vinyl acetate/crotonic acid/vinyl neodecanoate copolymer, vinyl acetate/crotonic acid copolymer, or mixtures thereof.

5. The composition of claim 4 wherein the cationic conditioning polymer is a Polyquaternium-10.

6. The composition of claim 4 wherein the cationic conditioning agent is cationic guar gum.

7. The composition of claim 5 wherein the ratio of amphoteric surfactant to hair styling polymer is approximately 4 to 1:0.5 to 1.

8. The composition of claim 7 wherein the ratio of amphoteric surfactant to hair styling polymer is approximately 1:1.

* * * * *